United States Patent
Svensson et al.

(10) Patent No.: US 12,336,888 B2
(45) Date of Patent: Jun. 24, 2025

(54) NEGATIVE PRESSURE WOUND THERAPY (NPWT) DRESSING

(71) Applicant: Mölnlycke Health Care AB, Gothenburg (SE)

(72) Inventors: Malin Svensson, Gothenburg (SE); Viktoria Skeppstedt, Västra Frölunda (SE); Malin Holmén, Gothenburg (SE); Elinor Bolyos, Landvetter (SE)

(73) Assignee: Mölnlycke Health Care AB, Mölndal (SE)

( * ) Notice: Subject to any disclaimer, the term of this patent is extended or adjusted under 35 U.S.C. 154(b) by 0 days.

(21) Appl. No.: 17/999,102

(22) PCT Filed: May 24, 2021

(86) PCT No.: PCT/EP2021/063756
§ 371 (c)(1),
(2) Date: Nov. 17, 2022

(87) PCT Pub. No.: WO2021/239661
PCT Pub. Date: Dec. 2, 2021

(65) Prior Publication Data
US 2023/0210699 A1   Jul. 6, 2023

(30) Foreign Application Priority Data
May 25, 2020   (EP) .................................... 20176287

(51) Int. Cl.
*A61F 13/05*   (2024.01)
*A61F 13/0203*   (2024.01)
*A61M 1/00*   (2006.01)

(52) U.S. Cl.
CPC .......... *A61F 13/05* (2024.01); *A61F 13/0223* (2013.01); *A61M 1/985* (2021.05)

(58) Field of Classification Search
CPC ............ A61F 13/05; A61F 2013/00655; A61F 2013/00604; A61M 1/60; A61M 1/71; A61M 1/90
See application file for complete search history.

(56) References Cited

U.S. PATENT DOCUMENTS 5,403,304 A    4/1995 Ishida
9,795,724 B2  10/2017 Whyte et al.
(Continued)

FOREIGN PATENT DOCUMENTS

CN   103841935       6/2014
CN   103841935 A     6/2014
(Continued)

OTHER PUBLICATIONS

International Search Report and Written Opinion were mailed on Jul. 22, 2021 by the International Searching Authority for International Application No. PCT/EP2021/063756 filed on May 24, 2021 and published as WO2021239661 (Applicant—Molnlycke Health Care AB) (10 pages).
(Continued)

*Primary Examiner* — Andrew J Mensh
*Assistant Examiner* — Meagan Ngo
(74) *Attorney, Agent, or Firm* — Ballard Spahr LLP

(57) ABSTRACT

Described is a negative wound therapy (NPWT) dressing that includes a backing layer and an adhesive skin contact layer, the adhesive skin contact layer being configured to detachably adhere the dressing to a dermal surface, wherein the backing layer includes a coupling member. The coupling member includes a tubing configured to connect the dressing to a negative pressure source and to a remote fluid collector.

18 Claims, 8 Drawing Sheets

(56) References Cited

U.S. PATENT DOCUMENTS

| | | | |
|---|---|---|---|
| 9,877,872 B2 | 1/2018 | Mumby et al. | |
| 10,231,878 B2 | 3/2019 | Hartwell et al. | |
| 11,738,136 B2 | 8/2023 | Nilsson et al. | |
| 2005/0080372 A1 | 4/2005 | Nielsen | |
| 2005/0182347 A1 | 8/2005 | Bishop et al. | |
| 2009/0177135 A1 | 7/2009 | Rogers et al. | |
| 2010/0305490 A1 | 12/2010 | Coulthard et al. | |
| 2012/0116334 A1* | 5/2012 | Albert | A61F 13/022 604/319 |
| 2012/0271257 A1 | 10/2012 | Coulthard et al. | |
| 2013/0172843 A1* | 7/2013 | Kurata | A61F 13/15731 156/60 |
| 2014/0276490 A1 | 2/2014 | Locke et al. | |
| 2014/0171888 A1 | 6/2014 | Croizat | |
| 2014/0249495 A1 | 9/2014 | Mumby et al. | |
| 2015/0051560 A1 | 2/2015 | Askem | |
| 2016/0030722 A1 | 2/2016 | Anderson et al. | |
| 2016/0262942 A1 | 9/2016 | Riesinger et al. | |
| 2016/0339226 A1 | 11/2016 | Sealfon | |
| 2017/0143552 A1 | 5/2017 | Hartwell et al. | |
| 2017/0189236 A1* | 7/2017 | Locke | A61F 13/01029 |
| 2018/0243139 A1* | 8/2018 | Szypka | A61F 13/01042 |
| 2019/0015258 A1* | 1/2019 | Gowans | A61F 13/05 |
| 2019/0151159 A1* | 5/2019 | Gowans | A61F 13/05 |
| 2019/0298579 A1 | 10/2019 | Moore et al. | |
| 2020/0085632 A1 | 3/2020 | Locke | |
| 2020/0337906 A1* | 10/2020 | Long | A61M 1/915 |
| 2021/0113748 A1* | 4/2021 | Rice | A61F 13/05 |
| 2021/0137743 A1 | 5/2021 | Hartwell et al. | |
| 2021/0187171 A1* | 6/2021 | Collinson | A61M 1/75 |
| 2021/0196525 A1* | 7/2021 | Bishop | A61F 13/0213 |
| 2022/0001212 A1* | 1/2022 | Bass | A61M 1/915 |
| 2022/0047799 A1* | 2/2022 | Quintanar | A61M 1/985 |
| 2022/0226559 A1* | 7/2022 | Locke | A61M 1/96 |

FOREIGN PATENT DOCUMENTS

| | | |
|---|---|---|
| CN | 103857365 | 6/2014 |
| CN | 109937056 | 6/2019 |
| DE | 102012223399 | 6/2014 |
| EP | 0214867 | 6/1991 |
| EP | 0541251 | 5/1993 |
| EP | 2253294 | 11/2010 |
| EP | 2529765 | 9/2013 |
| EP | 3320926 | 5/2018 |
| EP | 3320926 A1 | 5/2018 |
| GB | 0225544 | 12/2002 |
| GB | 2380945 A | 12/2002 |
| WO | WO 9608223 | 3/1996 |
| WO | WO1996008223 | 3/1996 |
| WO | WO 2004037334 | 5/2004 |
| WO | WO 2007/051599 | 5/2007 |
| WO | WO 2007113597 | 10/2007 |
| WO | WO 2008027449 | 3/2008 |
| WO | WO 2010141030 | 12/2010 |
| WO | WO 2011087871 | 7/2011 |
| WO | WO 2012156655 | 11/2012 |
| WO | WO 2013007973 | 1/2013 |
| WO | WO 2013015827 | 1/2013 |
| WO | WO 2013/029652 | 3/2013 |
| WO | WO 2015188003 | 12/2015 |
| WO | WO 2016079037 | 5/2016 |
| WO | WO 2017040074 | 3/2017 |
| WO | WO 2017087163 | 5/2017 |
| WO | WO 2017196888 | 11/2017 |
| WO | WO 2018086876 | 5/2018 |
| WO | WO 2018/158250 | 9/2018 |
| WO | WO 2018231815 | 12/2018 |
| WO | WO 2019040729 | 2/2019 |
| WO | WO 2019084087 | 5/2019 |
| WO | WO 2019089944 | 5/2019 |
| WO | WO 2019129581 | 7/2019 |
| WO | WO 2019171351 | 9/2019 |
| WO | WO 2020011691 | 1/2020 |
| WO | WO 2020055945 | 3/2020 |
| WO | WO 2020/078993 | 4/2020 |
| WO | WO 2020102214 | 5/2020 |
| WO | WO 2021239652 | 12/2021 |
| WO | WO 2021239653 | 12/2021 |
| WO | WO 2021239660 | 12/2021 |
| WO | WO 2021239661 | 12/2021 |

OTHER PUBLICATIONS

International Search Report and Written Opinion were mailed on Aug. 17, 2021 by the International Searching Authority for International Application No. PCT/EP2021/063755 filed on May 24, 2021 and published as WO 2021-239660 (Applicant—Molnlycke Health Care AB) (9 pages).

International Search Report and Written Opinion were mailed on Aug. 17, 2021 by the International Searching Authority for International Application No. PCT/EP2021/063748 filed on May 24, 2021 and published as WO2021239653 (Applicant—Molnlycke Health Care AB) (8 pages).

International Search Report and Written Opinion were mailed on Sep. 10, 2021 by the International Searching Authority for International Application No. PCT/EP2021/063747 filed on May 24, 2021 and published as WO2021239652 (Applicant—Molnlycke Health Care AB) (17 pages).

Notice of Opposition was issued for European Application No. 20176254.9 by the European Patent Office on Nov. 26, 2024 (40 pages).

\* cited by examiner

NEGATIVE PRESSURE WOUND THERAPY (NPWT) DRESSING

CROSS-REFERENCE TO RELATED APPLICATIONS

This application is a U.S. National Phase Application of International Application No. PCT/EP2021/063756, filed May 24, 2021, which claims priority to European Patent Application No. 20176287.9, filed May 25, 2020, each of which is hereby incorporated by reference in its respective entirety.

TECHNICAL FIELD

The present disclosure generally relates to a negative pressure wound therapy (NPWT) dressing. It also relates to a system and to a kit comprising such a dressing.

BACKGROUND

Negative pressure wound therapy (NPWT) is a technique that promotes healing of e.g. surgical, acute and chronic wounds by the application of a sub-atmospheric pressure to the wound, using a negative pressure pump. Wound healing is achieved by applying a negative pressure, such as vacuum through a dressing or a cover applied onto the wound. Excess wound exudate is thereby drawn out, which increases the blood flow to the area, and promotes the formation of granulation tissue. The NPWT technique also permits less outside disturbance of the wound and transports excess fluids away from the wound site.

The NPWT technique has, until now, mainly been applied to a patient while in a hospital environment. However, recent product development allows the technique to be used by a patient in a home environment.

In a hospital setting, the wound to be treated is typically an open cavity wound, which is first filled with a wound filler, such as a gauze or a foam. The wound may thereafter be sealed with an adhesive film dressing, and connected to a vacuum pump via a drain or a port. The size of the foam, gauze and/or the adhesive film may be adapted and cut depending on the size, shape or type of wound. The application procedure is typically carried out by a caregiver. The negative pressure pump used in such a system is typically of a large size and generally has a high capacity to deal with large amounts of wound exudate. In this type of systems, a fluid collection means, such as a canister, arranged remote from the dressing, is typically included. Wound exudate discharged from the wound is transferred by means of tubing to the canister for fluid collection.

In a home environment, a portable NPWT device, which may be carried around by the patient, is generally preferred. A portable NPWT device typically comprises an absorbent dressing configured to be connected to a negative pressure source by means of tubing. The pump used is in such devices is typically of a smaller size, and has a more limited capacity.

In most portable NPWT systems, the dressing serves as the sole means to collect wound exudate. If a large amount of wound exudate is handled, the dressing may become saturated quickly. This may negatively affect the dressing's ability to stay on the skin; i.e. the wear time of the dressing is reduced. As a result, the dressing needs to be discarded and replaced with a new dressing.

Accordingly, there is a need for improvement with respect to dressings for use in negative pressure wound therapy, particularly with respect to their ability to handle wound exudate such that the wear time of the dressing can be improved.

SUMMARY

In view of the above mentioned problems, it is an object of the present disclosure to provide improvements with respect to dressings for NPWT applications, particularly with respect to improving the wear time of the dressings and their ability to handle wound exudate such that the entire NPWT system and applied therapy works in an efficient manner.

According to a first aspect of the present disclosure, there is provided a negative pressure wound therapy (NPWT) dressing comprising a backing layer, an adhesive skin contact layer and an absorbent structure arranged between the backing layer and the adhesive skin contact layer; the adhesive skin contact layer being configured to detachably adhere the dressing to a dermal surface, wherein the backing layer comprises a coupling member configured to connect the dressing to a negative pressure source and to a remote fluid collection means, wherein the dressing comprises a liquid spreading layer arranged between the absorbent structure and the backing layer.

The present disclosure is based on the realization that the provision of a liquid spreading layer between the absorbent structure and the backing layer provides several advantages in terms of liquid handling and liquid distribution. The liquid spreading layer improves the spreading and distribution of wound exudate within the dressing, thereby forming a larger surface area from which exudate can evaporate from the dressing (through the backing layer). The larger surface area of the liquid spreading layer may thus act to more efficiently get rid of excess exudate and keep the wound site relatively dry.

In addition, the liquid spreading layer improves the distribution of potential "backflow" exudate; i.e. exudate flowing in the opposite direction (from the tubing to the dressing). This may for example occur if the dressing is disconnected from the negative pressure source and/or the remote fluid collection means. The liquid spreading layer secures that such back-flow of exudate is spread out on a large surface rather than flowing back towards the wound site in one spot.

The present disclosure is also based on the realization that an appropriate balance between distribution of wound exudate stored by the dressing, and wound exudate removed from the dressing (to the remote fluid collection means) can be achieved by means of the absorbent structure along with the liquid spreading. As a result, the wear time of the dressing is improved. The dressing of the present disclosure comprises a tubing configured to connect the dressing to a remotely arranged fluid collection means. In other words, wound exudate is both stored by and removed from the dressing. The dressing is designed to both secure efficient distribution of liquid within the dressing, but to also secure transfer of a substantial amount of liquid away from the dressing by means of the tubing.

In embodiments, the backing layer and at least a portion of the absorbent structure comprise an opening arranged underneath the coupling member, wherein the liquid spreading layer is void of an opening.

The opening serves to secure fluid communication between the wound site and the tubing of the dressing; and thereby also fluid communication between the wound site and the remotely arranged fluid collection means.

The liquid spreading layer is void of such an opening to prevent potential gelling particles and undesired larger particulate of the exudate from entering the tubing of the dressing. In the area underlying the coupling member of the dressing, the liquid spreading layer is configured to transfer liquid from within the dressing through the tubing and to the remote fluid collection means.

In embodiments, the liquid spreading layer is configured to extend across at least 90% of the surface area of the absorbent structure.

Accordingly, the liquid spreading layer is a continuous layer that extends across substantially the entire absorbent structure. This is to secure an efficient spreading of liquid across a large surface, and to improve the evaporation of liquid from the dressing.

In embodiments, the liquid spreading layer is hydrophilic and porous.

Accordingly, liquid may be transferred through the layer from within the dressing towards the tubing of the dressing, and thereby be transferred in an efficient manner to a remote fluid collection means, such as a canister.

In embodiments, the liquid spreading layer comprises a nonwoven.

The nonwoven imparts an appropriately balanced rigidity to the layer and to the dressing as such. A nonwoven liquid spreading layer has the ability to distribute fluid throughout the majority of the material and to transfer the exudate in a controlled manner to the tubing connecting the dressing with the remotely arranged fluid collection means.

In embodiments, the absorbent structure comprises superabsorbent particles in an amount of from 10 to 20 mg/cm2, preferably of from 13 to 17 mg/cm2.

The inventors have found that this range is beneficial in terms of achieving an appropriate balance between liquid being retained vs removed from the dressing by means of the tubing. Such a superabsorbent layer 103a absorbs exudate at a "reasonable" level. If too much SAP is included, the SAP layer may swell and absorb too much and too quickly. This may have the effect that the dressing serves as the sole or at least predominant means for fluid collection. In the context of the present disclosure, the balance between the remotely arranged fluid collection means, e.g. the canister and the dressing (which is also regarded as a fluid collection means) is preferably 50:50, e.g. at least 40:60 or 60:40. As mentioned hereinbefore, this balance is important to improve the wear time of the dressing.

In embodiments, the absorbent structure comprises a first liquid spreading layer, a superabsorbent layer and a second liquid spreading layer, wherein the superabsorbent layer is arranged between the first and the second liquid spreading layers.

The first liquid spreading layer is configured to absorb and distribute liquid flowing from the wound site. The first liquid spreading layer may distribute and spread the wound exudate evenly and over a large surface area such that it can be absorbed by the superabsorbent layer. The second liquid distribution layer distributes the exudate from the superabsorbent layer such that the exudate is spread over a large area before being evaporated from the backing layer or transported to the remote fluid collection means by means of the tubing.

The absorbent structure along with the liquid spreading layer overlying the absorbent structure is configured to optimize the distribution of wound exudate within the dressing, and to secure removal of a substantial amount of exudate by means of the tubing configured to connect the dressing with a remotely arranged fluid collection means.

The absorbent structure is designed to achieve an appropriate liquid distribution balance between the dressing and the remote fluid collection means, which both serve as fluid "compartments" for holding and storing liquids.

In embodiments, the absorbent structure is embossed.

The embossed absorbent structure improves the fluid handling properties of the dressing and contributes to a balanced and more controlled spreading of wound exudate from the dressing interior to the canister. Furthermore, the embossed absorbent structure allows the dressing to retain its shape and thinness, while also being pliable.

Typically, the backing layer and the adhesive skin contact layer are configured to extend beyond the periphery of the absorbent structure to form a border portion along the contour of the absorbent structure. In preferred embodiments, the adhesive skin contact layer comprises a plurality of apertures in the area underlying the absorbent structure, but is void of apertures in the area forming the border portion.

The apertures serve to improve the absorption of wound exudate into the dressing, and are therefore arranged in the area where absorption takes place. The area of the absorbent layer forming the border portion of the dressing is preferably void of apertures. This way, the adhesion against the skin is enhanced, and the stay-on ability of the dressing is thereby prolonged.

The dressing may further comprise a transmission layer arranged between the adhesive skin contact layer and the absorbent structure; the transmission layer comprising a spacer fabric.

The transmission layer facilitates the transmission of negative pressure from the negative pressure source to the wound site.

In embodiments, the dressing comprises a plurality of adhesive stripes between the absorbent structure and the transmission layer.

The adhesive stripes are configured to halt the flow of exudate towards the coupling member and the tubing. As mentioned hereinbefore, the dressing of the present disclosure preferably has a construction that enables a proper, and substantially equal balance between the dressing and the remotely arranged fluid collection means.

The adhesive stripes prevent exudate from flowing too quickly towards the remotely arranged fluid collection means such that the full absorbent capacity of the dressing can be utilized. The adhesive stripes may therefore contribute to the desired distribution of wound exudate between the dressing and e.g. a remotely arranged canister.

In embodiments, the backing layer has a moisture vapor transmission rate (MVTR) in the range of from 500 to 3500 g/m2/24 h, preferably in the range of from 600 to 2700 g/m2/24 h, as measured by NWSP070.4R0(15).

The moisture vapor transmission rate (MVTR) is the rate at which the backing layer (and thus also the dressing) allows moisture to evaporate. It is generally known that exuding wounds require absorbent dressings with backing layers having a significantly high moisture vapor transmission rate (MVTR). In contrast to what is known in the art, the present inventors have realized that a backing layer having a reduced MVTR is surprisingly associated with positive effects when such a dressing is applied in negative pressure wound therapy. A backing layer having an MVTR in the range of from 500 to 3500 g/m2/24 h improves the stability of the negative pressure therapy and system, and has a positive effect on the negative pressure source; i.e. the pump, which does not need to work as hard during therapy. The MVTR range specified above can still secure that excess moist is removed from the dressing in an efficient manner such that wound healing is stimulated. Furthermore, the provision of a liquid spreading layer below the backing layer may "compensate" for the reduced moisture vapor transmission rate (MVTR) of the backing layer.

In embodiments, the tubing of the dressing comprises a fluid conduit configured to remove fluid from the dressing and an air conduit configured to supply air to the fluid conduit and/or the dressing.

A small and controlled inflow of air may be beneficial to more efficiently draw fluid from the wound site and transport the fluid to the remotely arranged fluid collection means, e.g. the canister. The introduction of air may resolve potential exudate blockages or liquid columns formed in the tubing.

According to a second aspect, there is provided a negative pressure wound therapy (NPWT) system comprising:
- a negative pressure wound therapy (NPWT) dressing as described hereinbefore,
- a negative pressure source
- a remote fluid collection means fluidly connected to the negative pressure source and to the dressing.

In embodiments, the remote fluid collection means is a canister, wherein the canister and the negative pressure source are arranged within the same device; the device comprising a housing, in which the negative pressure source is arranged, wherein the canister is detachably connected to the housing.

The detachable configuration allows the user or caregiver to remove the canister and empty the collected liquid, and subsequently re-attach the canister to the negative pressure source again.

In embodiments, the NPWT system comprises means to supply air to the dressing at a rate of from 2 to 7 ml/min during operation.

As mentioned, a small and controlled inflow of air may be beneficial to more efficiently draw fluid from the wound site and transport the fluid to the remotely arranged fluid collection means, e.g. the canister. Air may be supplied to the dressing by means of tubing (e.g. the air conduit) in a controlled and at a relatively low rate such that problems relating to liquid columns and obstructions of the tubing are prevented. This way, the desired pressure level is transmitted to the wound site. In negative pressure wound therapy systems, there typically a static pressure difference introduced by gravity between the pressure inside the canister and the pressure at the wound site. This is due to the height difference between the canister and the wound site. A change in the static pressure may affect the ability to provide the correct level of negative pressure at the wound site. The provision of a small air flow or air leakage may resolve these problems. Furthermore, if too much air is introduced, this may negatively impact the stability of the system, and the pump is typically activated on a higher frequency.

According to third aspect, there is provided a kit comprising a negative pressure wound therapy (NPWT) dressing as described hereinbefore.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

Figure 1A:
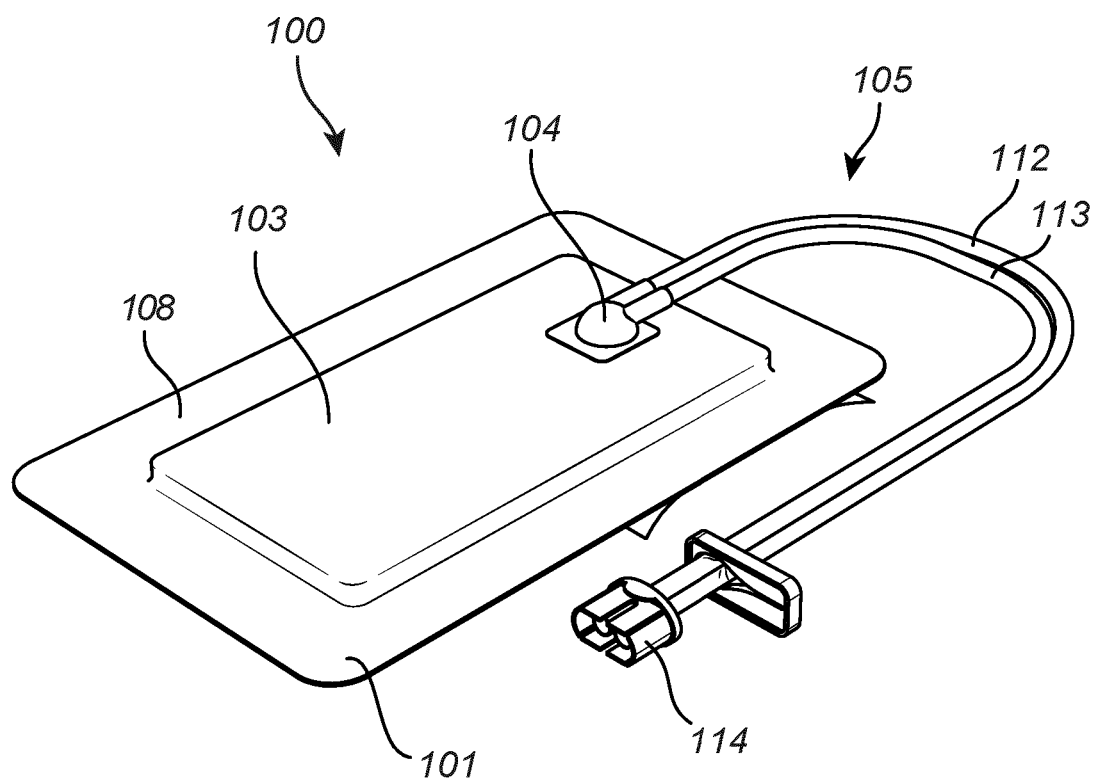
FIG. 1a illustrates a dressing according to an exemplary embodiment of the present disclosure.

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Figure 1B:
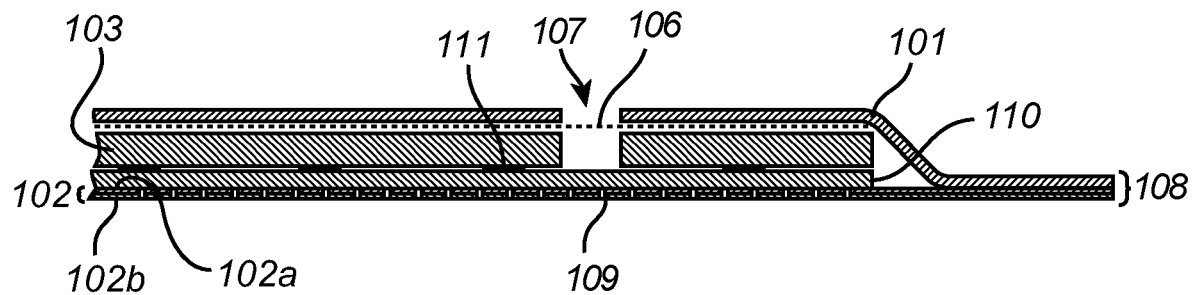
FIG. 1b illustrates a cross-sectional, partial view of the dressing of FIG. 1a, wherein the coupling member and the tubing is removed.

FIGS. 1a and 1b illustrate a negative pressure wound therapy (NPWT) dressing 100 in accordance with an exemplary embodiment of the present disclosure. The NPWT dressing 100 comprises a backing layer 101, an adhesive skin contact layer (see 102 in FIG. 1b) and an absorbent structure 103 arranged between the backing layer 101 and the adhesive skin contact layer; the adhesive skin contact layer being configured to adhere the dressing 100 to a dermal surface, wherein the backing layer 101 comprises a coupling member 104 comprising a tubing 105 configured to connect the dressing 100 to a negative pressure source and to a remote fluid collection means, wherein the dressing 100 comprises a liquid spreading layer 106 arranged between the absorbent structure 103 and the backing layer 101.

As used herein, the term "negative pressure wound therapy dressing" refers to a dressing for use in negative pressure wound therapy. In the context of the present disclosure, "negative pressure wound therapy" refers to a therapy utilizing a source of negative pressure (e.g. a vacuum pump) to remove excess fluid from a wound. The wound may be an open wound or it may be a closed wound; i.e. a surgically closed incision, and the term therefore also encompasses "topical negative pressure (TNP) therapy" applications, which is a term often used in the context of closed incisions.

The NPWT dressing 100 of the present disclosure comprises an absorbent structure, which may also be referred to as a "wound pad". The NPWT dressing is typically referred to as "bordered dressing". The backing layer 101 and the adhesive skin contact layer are arranged to extend beyond the contour of the absorbent structure 103 to form a border portion 108.

As used herein, the term "dermal surface" refers to the skin of the wearer. The skin may comprise a wound to be treated, such as an open or a closed wound.

The NPWT dressing 100 of the present disclosure is adapted for use in an NPWT system comprising a remote fluid collection means. As used herein, the term "remote fluid collection means" means that the fluid collection means is arranged at a distance from the dressing, e.g. between the dressing and the negative pressure source or is connected to the negative pressure source. In embodiments, the negative pressure source and the fluid collection means are arranged in the same NPWT device.

Figure 1C:
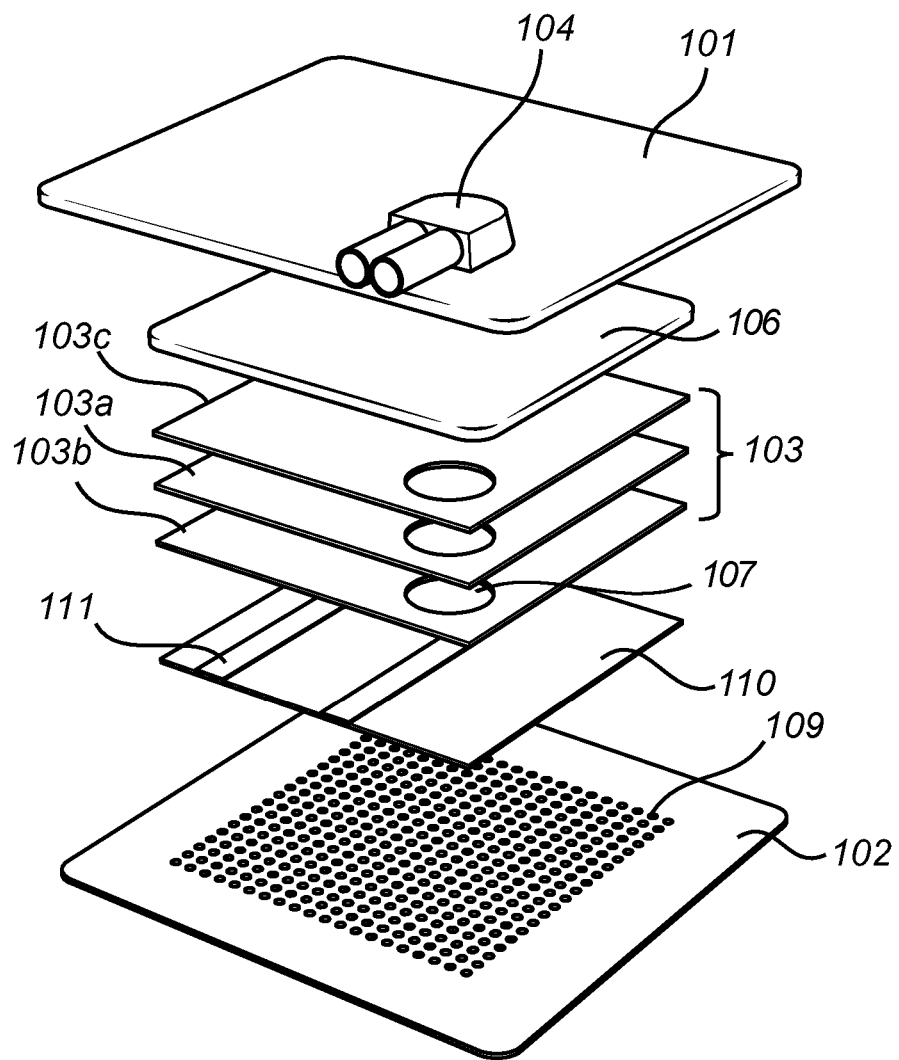
FIG. 1c illustrates a split view of a dressing according to an exemplary embodiment of the present disclosure.

As best illustrated in FIG. 1b and FIG. 1c, the backing layer 101 and at least a portion of the absorbent structure 103 comprises an opening 107 arranged underneath the coupling member 104; the liquid spreading layer 106 being void of an opening.

The opening 107 ensures fluid communication between the wound site and the remotely arranged fluid collection means. It also enables transmission of negative pressure to the wound site. The coupling member 104 overlies the opening 107 in the backing layer (as best illustrated in FIG. 1c). In FIG. 1c, the absorbent structure 103 comprises three layers, each of which comprises an opening. It is however also conceivable that an opening is provided in only one or in two layers of the absorbent structure 103.

The fact that the liquid spreading layer 106 does not contain any opening prevents gelling particles and undesired larger particulate from entering the tubing 105 of the dressing 100.

The liquid spreading layer 106 is configured to extend across at least 90% of the surface area of the absorbent structure 103.

Preferably, the liquid spreading layer 106 is configured to extend across the entire surface area of the absorbent structure 103. Accordingly, the liquid spreading layer 106 and the absorbent structure 103 have the same outer dimensions and cross sectional areas.

The liquid spreading layer 106 is configured to improve the spreading of wound exudate and to create a larger surface area from which moisture can evaporate through the backing layer 101.

The liquid spreading layer 106 is preferably a hydrophilic and porous layer. This way, exudate can efficiently be transferred from the wound site, through the liquid spreading layer 106 to the tubing 105.

The liquid spreading layer 106 may be a fibrous material. In embodiments the liquid spreading layer 106 comprises a nonwoven.

A nonwoven liquid spreading layer 106 has the ability to distribute fluid throughout the majority of the material and to transfer the exudate in a controlled manner to the tubing 105 connecting the dressing with the remotely arranged fluid collection means.

The liquid spreading layer 106 aids in driving the fluid away from the wound site and from the absorbent structure 103, while at the same time securing that the maximum capacity of the absorbent dressing is utilized.

The liquid spreading layer 106 is also beneficial to spread potential exudate flowing from the tubing 105 towards the dressing; i.e. exudate flowing in the "wrong" direction. Back-flow of exudate may occur if the person wearing the dressing disconnects the dressing from the negative pressure source and the fluid collection means. For example, the patient may disconnect the NPWT dressing if he/she is to take a shower or change clothes. The liquid spreading layer 106 secures that such back-flow of exudate is spread out rather than flowing back towards the wound site in one spot. This way, the wound site can be kept relatively dry.

The liquid spreading layer 106 may comprise a meltblown, spunbond or a spunlaced nonwoven. Examples of suitable polymers for use in the nonwoven are polyethylene, polyesters, polypropylene and other polyolefin homopolymers and copolymers. For example, nonwoven webs comprising thermoplastic fibers of polypropylene and polyethylene fibres or mixtures thereof may be used. The webs may have a high content of thermoplastic fibres and contain at least 50%, e.g. at least 70% thermoplastic fibres. The nonwoven may be a mixture of polyester and viscose, e.g. in a 70:30 ratio. The basis weight of the nonwoven may be in the range of from 10 to 80 g/m2, e.g. of from 20 to 50 g/m2. The liquid spreading layer may also be a spunbond-meltblown or spunbond-meltblown-spunbond (SMS) web.

The liquid spreading layer 106 preferably has the capacity to absorb wound exudate flowing from the absorbent structure. In embodiments, the liquid spreading layer 106 has an absorption capacity of at least 10 g/g, as measured by the standard test method NWSP 10.1.

In embodiments, the absorbent dressing has a retention capacity of from 300 to 700 mg/cm2, preferably from 400 to 600 mg/cm2, as measured by the test method described in Example 2.

The inventors have found that the retention capacity of the dressing is important to secure that a balanced distribution of liquid between the two fluid collection means (the dressing and e.g. the canister) is achieved. The balanced distribution of liquid between the two fluid collection means is key for optimizing the wear time of the dressing and also to secure that the maximum capacity of the dressing is utilized.

The absorbent structure 103 is configured to absorb wound exudate and to distribute such wound exudate in an efficient manner. The absorbent structure 103 may function as a temporary reservoir to retain and distribute exudate, while also securing a controlled transport of liquid transport towards the tubing 105 (and the fluid collection means arranged remote from the dressing).

The absorbent structure 103 may comprise one or a plurality of layers, wherein at least one of the layers comprises a superabsorbent layer comprising superabsorbent polymers (SAP).

A "superabsorbent polymer" or "SAP" is a polymer that can absorb up to 300 times its own weight in aqueous fluids. Superabsorbent polymers are constituted by water-swellable and water insoluble polymers capable of absorbing large quantities of fluid upon formation of a hydrogel. The superabsorbent polymers for use in accordance with the present disclosure may be inorganic or organic crosslinked hydrophilic polymers, such as polyvinyl alcohols, polyethylene oxides, crosslinked polyacrylates and the like. Typically, the superabsorbent (SAP) comprise sodium acrylate. The SAP material may be in the form of particles, fibers, flakes or similar. Preferably, the SAP material is in the form of superabsorbent polymer (SAP) particles. The size of the superabsorbent particles may be in the range of from 45 to 850 µm, preferably from 150 to 600 µm.

The absorbent structure may comprise superabsorbent particles in an amount of from 10 to 20 mg/cm2, preferably of from 13 to 17 mg/cm2.

This range is beneficial as it allows the absorbent structure to absorb exudate at a "reasonable" level. If too much SAP is included, the SAP layer may swell and absorb too much and too quickly. This may have the effect that the dressing serves as the sole or at least predominant means for fluid collection. In the context of the present disclosure, the balance between the dressing and the remotely arranged fluid collection means, e.g. the canister is preferably of from 40:60 to 60:40. The inventors have found that such distribution may be maintained for up to 9 days of therapy without needing to replace the dressing (see Example 1).

Preferably, the absorbent structure comprises at least one superabsorbent layer 103a and at least one liquid spreading layer.

As illustrated in FIG. 1c, the absorbent structure 103 comprises three layers 103a-c.

At least one of these layers is a liquid spreading layer. In embodiments, the lowermost layer of the absorbent structure 103 is a liquid spreading layer 103b. Exudate entering the liquid spreading layer 103b from the wound site is evenly distributed before entering the other layer(s) of the absorbent structure 103, thereby creating a larger surface area towards the superabsorbent layer 103a and other layer(s) of the absorbent structure 103, if present.

The absorbent structure may comprise a first liquid spreading layer 103b, superabsorbent layer 103a and a second liquid spreading layer 103c, wherein the superabsorbent layer 103a is arranged between the first and the second liquid spreading layers (103b, 103c).

The first and/or second liquid spreading layer may comprise any material having the ability to distribute the exudate in an efficient manner. For example, the first and/or second liquid spreading layer comprises a nonwoven material.

Preferably, the first liquid spreading layer 103b is arranged below the superabsorbent layer 103a and has a greater liquid spreading capacity than the second liquid spreading layer 103c. An absorbent structure with a liquid spreading gradient is thus achieved, which impacts the ability of the absorbent structure 103 to retain, and remove, respectively, liquid from and within the dressing.

For example, the first liquid spreading layer 103b may comprise a nonwoven. The nonwoven may have a grammage in the range of from 20 to 50 gsm, e.g. from 30 to 40 gsm. The thickness of the liquid spreading layer 103b may be from 0.2 to 1.2 mm, e.g. from 0.2 to 0.6 mm. The thickness is measured in dry conditions.

The second liquid spreading layer 103c may be a tissue or a nonwoven layer. Typically, the spreading capability of the upper layer 103c is lower than the spreading capability of the lower liquid spreading layer 103b.

The layer 103c also serves to prevent leakage of SAP particles from the superabsorbent layer 103a. The SAP particles of the superabsorbent layer 103a chemically bind exudate entering the superabsorbent layer 103a, and thereby forms an aqueous gel. The layer 103c prevents gelling particles from moving towards the backing layer 101 and towards the coupling member 104 comprising the tubing 105. Undesirable blockage of gel particles within the tubing 105 is thereby prevented. Preferably, the layer 103c is a liquid spreading layer and serves to create a larger indirect surface of distributed liquid towards the backing layer 101 of the dressing 100. The layer 103c or 103b may also serve as a "support layer" and act as a carrier during the manufacturing process.

The various layers of the absorbent structure create a complex liquid absorption and retention structure and an improved liquid distribution is observed. Particularly a controlled distribution of exudate being retained, and removed, respectively, has been observed.

The absorbent structure 103 is preferably embossed. In other words, the surface(s) of the absorbent structure 103 is structured and may comprise a plurality of indentations and elevations (not shown). This is beneficial since an absorbent structure 103 comprising a plurality of layers may become stiff and thick as the basis weight increases. The embossing allows the absorbent structure to retain its shape and thinness, while being pliable.

The superabsorbent layer 103a may be an airlaid superabsorbent layer. In embodiments, the airlaid superabsorbent layer 103a comprises superabsorbent particles, cellulosic fibers and bicomponent fibers.

For example, the airlaid superabsorbent layer may comprise:
30-50%, preferably 35-50% by weight of superabsorbent particles
30-50%, preferably 40-50% by weight of cellulosic fibers
3-10%, preferably 5-8% by weight of bicomponent fibers
3-8% by weight of polyethylene.

Such a superabsorbent layer allows for improved liquid handling properties and a proper distribution of liquid. Furthermore, it prevents gel blocking and prevents the absorbent structure from collapsing when a large amount of fluid is handled.

The bicomponent fibers act as a bonding agent, providing integrity to the SAP layer, especially in the wet state. The biocomponent fibers may be made of polyethylene and polyethylene terephthalate (PE/PET).

The thickness of the superabsorbent layer 103a may be from 0.8 to 2.5 mm, e.g. from 1.4 to 2.2 mm, e.g. from 1.8 to 2.0 mm. The thickness is measured in dry condition.

In embodiments, the absorbent structure 103 comprises additional layers

The backing layer 101 and the adhesive skin contact layer 102 are configured to extend beyond the periphery of the absorbent structure 103 to form a border portion 108 along the contour of the absorbent structure 103. In other words, the dressing comprises a pad portion and a border portion 108. The pad portion comprises the absorbent structure 103 and the liquid spreading layer 106. The border portion 108 is therefore configured to extend beyond the periphery of the liquid spreading layer 106 as well. In embodiments, the pad portion comprises additional layers.

In preferred embodiments, the adhesive skin contact layer 102 comprises a plurality of apertures 109 in the area underlying the absorbent structure 103, but is void of apertures in the area forming the border portion 108.

The lack of apertures in the border portion of the dressing is beneficial to improve the adhesion at the border portion 108 of the dressing and thereby improve the stay-on ability of the dressing.

The adhesive skin contact layer 102 is the lowermost layer of the dressing. The adhesive skin contact layer 102 is configured to detachably adhere the dressing to a dermal surface. In other words, the adhesive skin contact layer 102 is configured to contact the skin or the wound of a wearer. This layer may also be referred to as a "wound contact layer" or a "skin contact layer".

The adhesive skin contact layer 102 preferably comprises a silicone based adhesive; i.e. a silicone gel. An adhesive skin contact layer comprising a silicone gel is skin-friendly and easy to remove without causing trauma. It is sufficiently adherent to skin such that the dressing stays in place, yet is configured to maintain its adherence with repeated removal and re-application.

As illustrated in FIG. 1b, the adhesive skin contact layer 102 may comprise two layers. For example, the adhesive skin contact layer 102 may comprise a polymer based film 102a and a silicone gel layer 102b; the silicone gel layer 102b being configured to contact the skin of a wearer.

The polymer based film 102a is preferably a breathable film and may comprise e.g. polyethylene, polyamide, polyester or polyurethane. Preferably, the polymer based film comprises polyurethane. The thickness of the polyurethane film may be from 15 to 100 µm, e.g. from 20 to 80 µm, preferably from 20 to 60 µm.

Examples of suitable silicone gels for use in the adhesive skin contact layer 102 and/or in the silicone gel layer 102b include the two component RTV systems, such as Q72218 (Dow Corning), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive skin contact layer is typically at least 20 µm. The thickness of the adhesive skin contact layer may be from 100 to 200 µm.

The adhesive skin contact layer 102 comprises a plurality of apertures 109. The apertures 109 extend through the polymer based film 102a (if present) and the silicone gel layer 102b.

The dressing 100 may further comprise a transmission layer 110 arranged between the adhesive skin contact layer 102 and the absorbent structure 103.

The transmission layer 110 may comprise a foam, a needled nonwoven, a through air bonded nonwoven or a spacer fabric. The transmission layer 110 is not limited to a particular material, but any material configured to ensure that negative pressure can be transmitted to the wound area during both wet and dry conditions can be used. The transmission layer 110 secures that fluid can be transported away from the wound site into the absorbent structure such that the skin can remain relatively dry.

Preferably, the transmission layer 110 comprises a spacer fabric. The spacer fabric is a three dimensional material that is often utilized in negative pressure wound therapy (NPWT) dressings.

In embodiments, the spacer fabric layer has a thickness of from 1.5 to 4 mm, e.g. from 2 to 3 mm. The thickness is measured in dry condition. The basis weight of the spacer fabric may be from 150 to 500 gsm, e.g. from 200 to 350 gsm.

The spacer fabric layer 110 typically comprises a top layer and a bottom layer and an interconnecting layer of pile filaments between the top layer and the bottom layer. The interconnecting layer of pile filaments may have a fineness of 200 to 500 denier, e.g. from 250 to 350 denier.

The spacer fabric layer 110 is resistant to compression and is configured to withstand pressures exerted on the dressing during use. After a compressive force has been exerted to the dressing, the transmission layer 110 is configured to return to its original shape immediately after removal of the force.

In embodiments, the dressing comprises a plurality of adhesive stripes 111 between the transmission layer 110 and the absorbent structure 103.

The adhesive stripes 111 are configured to halt the flow of exudate towards the coupling member 104 and the tubing 105. As mentioned hereinbefore, the dressing 100 of the present disclosure preferably has a construction that enables a proper, and substantially equal balance between the dressing and the remotely arranged fluid collection means.

When wound exudate flowing from the wound site, it is first handled by the transmission layer 110, and upon exit from the transmission layer 110, the adhesive stripes 111 serve to direct the exudate into the overlying absorbent structure 103, rather than flowing directly towards the tubing 105. The provision of the adhesive stripes 111 may therefore contributes to the desired distribution of wound exudate between the dressing and the remotely arranged canister. The area underneath the opening 107 is preferably free from any adhesive stripes. This is to prevent clogging and obstruction of the tubing 105 and the coupling member 104.

A "plurality of stripes" means that the dressing comprises at least two adhesive stripes. For example, the dressing may comprise from 2 to 10, e.g. from 2 to 6 adhesive stripes depending on the size of the dressing.

The adhesive stripes 111 may be arranged across the width of the dressing 100. The adhesive stripes may thus be arranged to extend between the lateral edges of the transmission layer 110 and/or the absorbent structure 103. The stripes are preferably arranged orthogonal to the flow path of exudate towards the tubing 105. Accordingly, the adhesive stripes 111 are arranged such that exudate flowing into the dressing must always meet an adhesive stripe 111 when flowing towards the tubing 105.

The adhesive is preferably a hot-melt adhesive. The width of the adhesive stripes may be in the range of from 3 to 25 mm, e.g. from 5 to 15 mm, e.g. from 6 to 10 mm.

The distance between the adhesive stripes 111 may be from 10 to 50 mm, e.g. from 15 to 30 mm. The distance between the adhesive stripes 111 may depend on the size and shape of the dressing 100.

The transmission layer 110, the absorbent structure 103 and the liquid spreading layer 106 may collectively be referred to as the wound pad of the dressing.

In embodiments, the backing layer 101 has a moisture vapor transmission rate (MVTR) in the range of from 500 to 3500 g/m2/24 h, preferably in the range of from 600 to 2700, such as from 1400 to 2600 g/m2/24 h as measured by NWSP070.4R0(15).

The backing layer 101 is the outermost layer of the dressing and is configured to face away from the skin of a wearer.

The "moisture vapor transmission rate (MVTR)" is the rate at which the backing layer allows moisture to permeate from the backing layer. The moisture vapor transmission rate is measured by the standard method NWSP070.4R0(15). The MVTR is measured at a temperature of 38° C.

This range has surprisingly been shown to yield positive effects when the dressing is used in negative pressure wound therapy. A more stable therapy with less frequent activations of the negative pressure source is observed, and yet, the exudate fluid collected within the dressing can be successfully evaporated from the backing layer to the surrounding. Overall, this has positive effects in terms of battery consumption, reduction of noise and a prolonged and more stable wound therapy.

When the dressing 100 of the present disclosure is applied in an NPWT system comprising a remotely arranged fluid collection means, wound exudate is drawn from the wound site to the fluid collection means by means of the tubing 105.

The continuous (or intermittent) removal of exudate through the tubing requires the NPWT source; i.e. the vacuum pump to become activated at regular intervals. However, if the pump is activated too often, and at a rate that is "more than necessary", this has negative consequences for noise as well as battery consumption. With the dressing 100 of the present disclosure, a reduction of pump activations has been observed by at least 26%, as demonstrated in Example 4 hereinafter.

In embodiments, the backing layer 101 has a tensile strength in the machine direction (MD and/or cross-machine direction (CD) of from 30 to 70 MPa, preferably from 35 to 55 MPa, as measured by ISO 527-3/2/200. The tensile strength is measured with 15 mm wide strips.

Preferably, the backing layer 101 has sufficient "strength" to withstand the forces inflicted on the backing layer during movement of the patient, yet allowing for pliability and a sufficient degree of stretchability.

The inventors have found that the tensile strength of the backing layer also has an impact in providing a stable and reliable therapy. The backing layer should be rigid enough to prevent tearing or rupture of the backing layer during movement of the patient. For instance, the edges of the absorbent structure may be particularly vulnerable to rupture since the thicker absorbent structure may chafe against the backing layer at the edges. If perforations or slits are formed in the backing layer, this may be associated with an undesirable air leak into the dressing and the system. Consequently, the stability of the therapy and the system is impaired. However, the backing layer must still be sufficiently pliable to allow the dressing to adapt to the movement of a user or to the bending of a joint, such as a knee.

The backing layer 101 typically comprises a thermoplastic elastomer. A thermoplastic elastomer has the ability to be stretched to moderate elongations, and upon the removal of stress, return to its original shape. Examples of suitable materials comprising thermoplastic elastomer include polyurethane, polyamide and polyethylene.

The backing layer may also be a laminate of polyester based nonwoven materials and at least one polyurethane film.

Preferably, the backing layer comprises a thermoplastic polyurethane.

The thickness of the backing layer may be in the range of from 10 to 40 μm, preferably from 15 to 30 μm.

The backing layer may 101 comprise at least one film. For example it may comprise more than one films. In embodiments, the backing layer is a laminate formed by two or more films. A thin layer of adhesive, such as a polyacrylate adhesive, may be applied to the backing layer to attach the backing layer to the adhesive skin contact layer or, where present, an absorbent structure or any other layer of the dressing. Within the context of the present disclosure, the backing layer 101 comprises the at least one film of thermoplastic elastomer and an adhesive (e.g. polyacrylate) applied thereon. The adhesive may be applied in a continuous or discontinuous pattern.

As illustrated in FIG. 1a, the tubing 105 comprises a fluid conduit 112 configured to remove fluid from the dressing and an air conduit 113 configured to supply air to the fluid conduit 112 and/or the dressing 100. Furthermore, the tubing 105 is configured to transmit negative pressure to the dressing and to the wound site.

The tubing 105 and/or the coupling member 104 may be of any suitable flexible tubing fabricated from elastomeric and/or polymeric materials. The tubing is attached to the coupling member 104. In embodiments, the tubing 105 is firmly attached to the coupling member 104. In alternative embodiments, the tubing 105 is detachably attached to the coupling member 104.

The coupling member 104 typically comprises an attachment portion configured to be attached to the backing layer of the dressing. The coupling member may be adhesively attached to the backing layer. The coupling member may also comprise a fluid inlet and a fluid outlet configured to be connected to the tubing 105; i.e. to the air conduit 113, and to the fluid conduit 112, respectively.

The coupling member may have the construction as defined in EP application No. 13152841.6.

In embodiments, the distal end of the tubing 105 is connected to a first connector portion 114. The first connector portion 114 is configured to be connected to a second connector portion associated with the remote fluid collection means; i.e. the canister and, in embodiments, to the negative pressure source (see e.g. FIG. 3 where a second connector portion 123 associated with the canister tubing is illustrated). Furthermore, the tubing 105 is configured to transmit negative pressure to the dressing and to the wound site FIG. 2 conceptually illustrates a negative pressure wound therapy (NPWT) system according to the present disclosure.

The negative pressure wound therapy (NPWT) system 200 comprises an NPWT dressing 100 in accordance with the present disclosure. The dressing 100 is applied to the knee of a patient 115.

The NPWT system 200 comprises
a negative pressure wound therapy (NPWT) dressing 100 as described hereinbefore,
a negative pressure source
a remote fluid collection means 117 fluidly connected to the negative pressure source and to the dressing 100.

The negative pressure source is a negative pressure pump adapted for establishing a negative pressure when the negative pressure pump is in an active state. The negative pressure pump may be any type of pump that is biocompatible and maintains or draws adequate and therapeutic vacuum levels. Preferably, the negative pressure level to be achieved is in a range between about −20 mmHg and about −300 mmHg. In embodiments of the present disclosure, a negative pressure range between about −80 mmHg and about −180, preferably between about −100 and −150 mmHg, more preferably between −110 and −140 mmHg is used. In embodiments, the negative pressure pump is a pump of the diaphragmatic or peristaltic type.

As used herein, the term "fluidly connected" should be interpreted broadly and may comprise e.g. any form of tubing, conduits, or channels providing a fluid connection/communication between the remote fluid collection means 117 and the negative pressure source and the dressing 100.

The remote fluid collection means 117 may be any kind of fluid container, e.g. a canister. Alternatively, it may be an absorbent material present within the tubing of the NPWT dressing or NPWT system or a dressing or absorbent structure arranged between the dressing of the present disclosure and the canister. Typically, the remote fluid collection means 117 is a canister.

Figure 2:
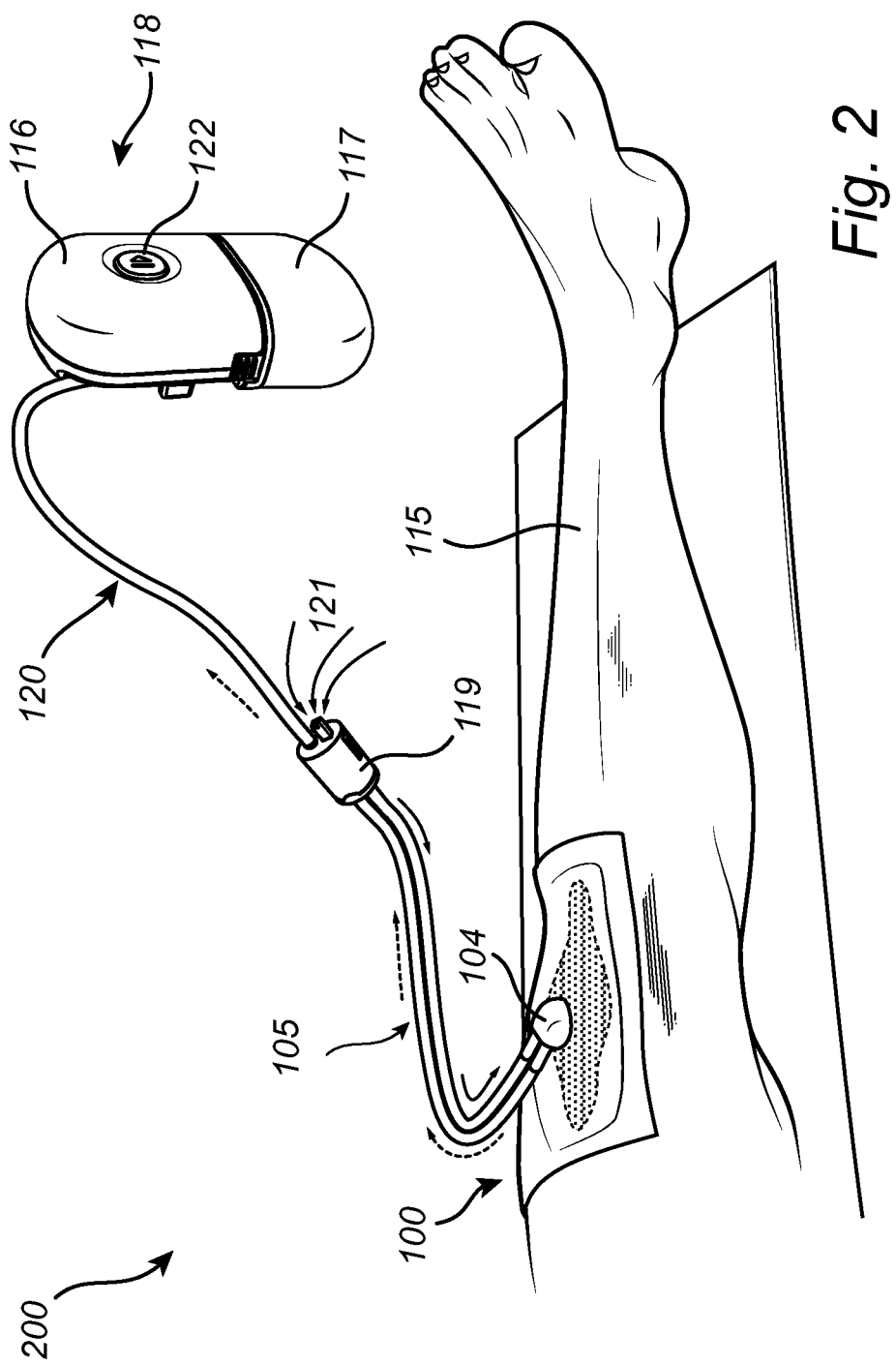
FIG. 2 conceptually illustrates a negative pressure wound therapy (NPWT) system according to an exemplary embodiment of the present disclosure.

In FIG. 2, the negative pressure source is comprised within a housing 116 of a portable negative pressure wound therapy (NPWT) device 118. The canister is preferably detachably connected to the housing 116.

In other words, the canister 117 is releasably connected to the housing 116. The detachable connection may be by conventional means including a friction fit, bayonet coupling, snap fit, barbed connector, or the like. The detachable configuration allows the user or caregiver to remove the canister 117 and empty the collected liquid, and subsequently re-attach the canister 117 to the housing 116 again.

The canister 117 may be formed from e.g. molded plastic or the like. The canister 117 is preferably at least partly transparent/translucent to permit viewing into the interior of the canister 117 to assist the user in determining the remaining capacity of the canister 117.

For example, an inner volume of the canister 117 is between 30-300 ml, e.g between 40 and 150 ml. The inner volume of the canister 103 may vary depending on the type of wound. In embodiments, the canister 117 comprises a liquid absorbent material. In a possible embodiment at least 75% of the inner volume of the canister 103 is occupied with a liquid absorbent material.

The NPWT device 118 may be connected to the dressing 101 by means of the tubing 105. In the embodiment illustrated in FIG. 2, the NPWT system comprises a connector unit 119 at a position between the dressing 100 and the NPWT device 118. The connector unit 119 may comprise the first connector portion (denoted 114 in FIG. 1) and the second connector portion (see 123 in FIG. 3). The connector portions 114 and 123 are preferably detachably connected such that the dressing can be easily disconnected from the NPWT device 118. This is beneficial in portable NPWT systems as the user may decide to disconnect the dressing from the device 118 when he/she is going to take a shower or for some other reason.

In FIG. 2, the tubing 105 is a double conduit, whereas the tubing 120 between the NPWT device 118 and the connector unit 119 is a single conduit. The NPWT system is by no means limited to such a construction, but may comprise a single conduit or a double conduit between the NPWT device 118 and the dressing 100. The NPWT system is also not limited to the use of a connector unit 119. The tubing 105 may, in embodiments be configured to extend all the way to the NPWT device 118.

The NPWT system 200 preferably comprises means to supply air to the dressing at a rate of from 2 to 7 ml/min during operation.

Preferably, the means to supply air to the dressing is configured to supply air at a rate of from 2-7 ml, preferably of from 3-5 ml at a negative pressure of from −80 to −180 mmHg, preferably of from −100 to −150 mmHg, more preferably of from −110 to −140 mmHg.

In the NPWT system 100 illustrated in FIG. 2, ambient air is introduced into the system by means of the connector unit 119 (illustrated by the arrows 121). For example, the first and/or the second connector portion (114 and 123) comprises an air filter (not shown) configured to control the supply of air into the dressing 100 and/or into the tubing 105. The first and/or the second connector portion (114 and 123) may e.g. comprise an air inlet port, wherein the air filter is arranged.

The air filter preferably comprises a hydrophobic and porous material, wherein the size of the pores is within the range of from 2 to 20 μm, preferably in the range of from 5 to 12 μm. The pore size of the filter is measured in a non-compressed state.

The air filter preferably comprises polyethylene, preferably sintered polyethylene.

A sintered polyethylene filter has a repeating linear molecular structure —CH2-CH2. The structure is inert with strong molecular bonds, and is characterized by improved chemical resistance, light weight, thermoplasticity and good filtering properties. A sintered polyethylene filter is also environmentally friendly as it produces no toxic waste and can be washed off and re-used.

The air filter secures that the supply of air is in the range of from 2-7 ml/min during operation, e.g. at a negative pressure of −80 mmHg to −150 mm Hg, e.g. from −100 mmHg to −130 mmHg.

It should be noted that air may be introduced into the system in alternative ways, and an air filter may be provided at alternative positions in the system. The regulation of air supply may, in embodiments, be controlled by the NPWT device 118.

During use, the dressing 100 is arranged at a wound site of the user/patient, forming a sealed space. The tubing (105 and 120) is provided to fluidly connect the dressing 100 to the NPWT device 118, e.g. to an inlet port of the NPWT device 118. The NPWT device 118 is then activated, e.g. by the user/patient, by pressing the start/pause button 122. The negative pressure pump is thereby activated. When activated, the negative pressure pump will start to evacuate air through the canister 117, the tubing (120 and 105) and the sealed space formed by the dressing 100. Accordingly, the negative pressure will be created within the sealed space. In case a liquid has been formed at the wound site, this liquid from the wound site may at least partly be "drawn" from the wound site, through the tubing (105 and 120), and into the canister 117. The amount of liquid; i.e. exudate that is drawn from the wound and collected in the canister 117 will depend on the type of wound that is being treated as well as the type of wound dressing used. Within the context of the present disclosure, a substantially equal balance between liquid distribution is desired. A suitable filter member (not shown) may be arranged between the canister 117 and the negative pressure pump to ensure that no liquid is allowed to pass to the negative pressure pump from the canister 117.

The canister 117 may comprise an inlet port for allowing connection to the tubing 120. The connection between the inlet port and the tubing 120 is preferably a sealed connection, thus ensuring that no leakage is formed at the inlet port during normal operation of the NPWT device 118. The tubing 120 is preferably releasably connected to the inlet port through conventional means including a friction fit, bayonet coupling, snap fit, barbed connector, or the like. A similar sealed is formed between the canister 117 and the negative pressure pump.

Figure 3:
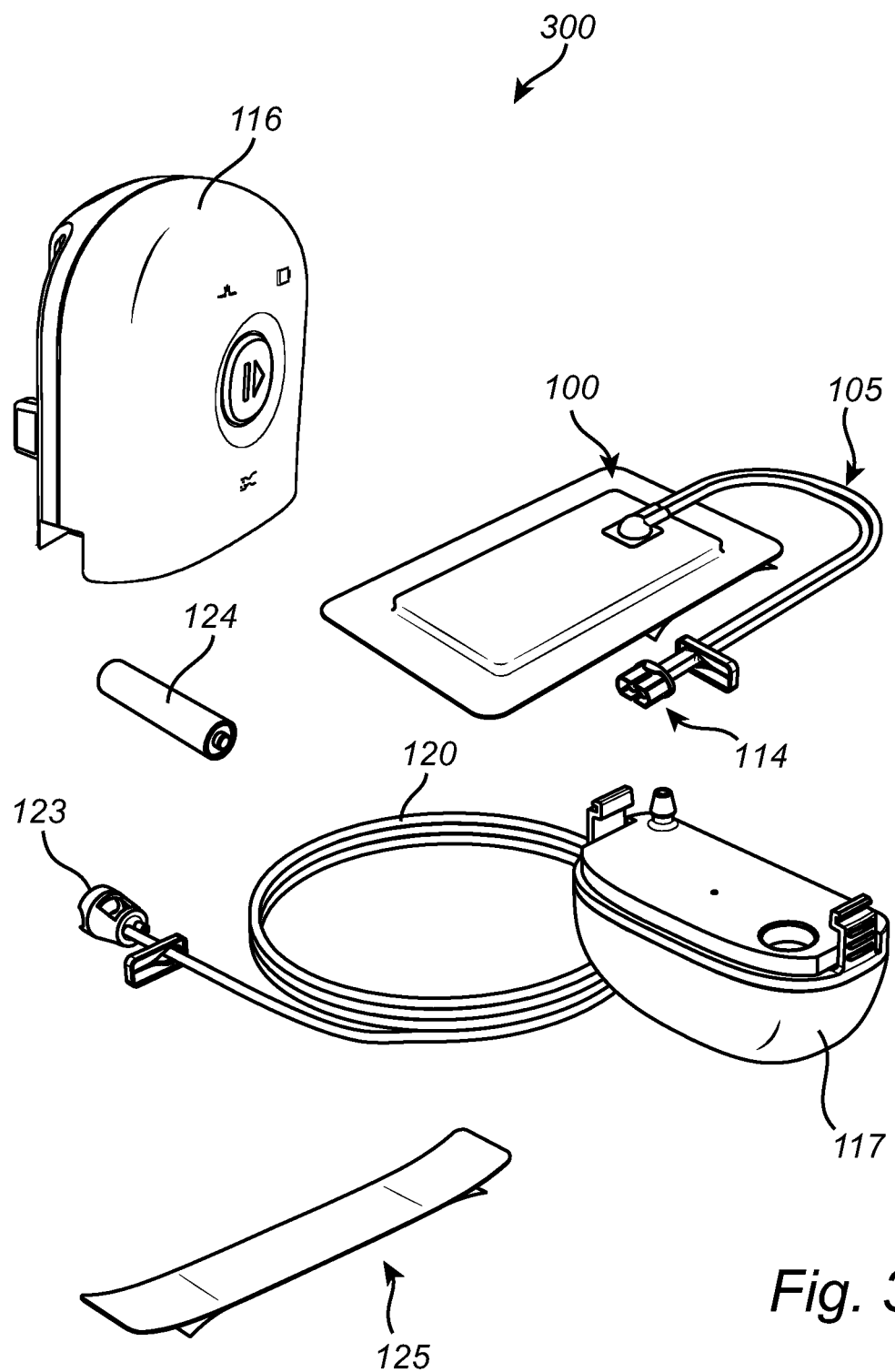
FIG. 3 illustrates a negative pressure wound therapy (NPWT) kit according to an exemplary embodiment of the present disclosure.

FIG. 3 illustrates a kit 300 according to an exemplary embodiment. The kit 300 comprises at least one NPWT dressing 100 as described hereinbefore.

The dressing comprises a tubing 105. Preferably the tubing 105 is pre-attached to the dressing, e.g. by means of a coupling member 104 attached to the backing layer of the dressing 100. The fact that the tubing 105 is pre-attached allows for a quick assembly of the components of the system/kit.

The distal end of the tubing 105 is connected to a first connector portion 114. The kit may further comprise a negative pressure source arranged within a housing 116. The kit may also comprise a canister 117. The canister may comprise a second tubing 120. The distal end of the second tubing 120 may comprise a second connector portion 123. The second connector portion 123 is configured to be connected to the first connector portion 114 associated with the tubing 105 of the dressing 100. The kit 300 may comprise additional components such as additional batteries 124 for powering the NPWT device 118 and adhesive strips 125 for improving the adhesion between the border portion of the dressing to the skin of a wearer.

Figure 4:
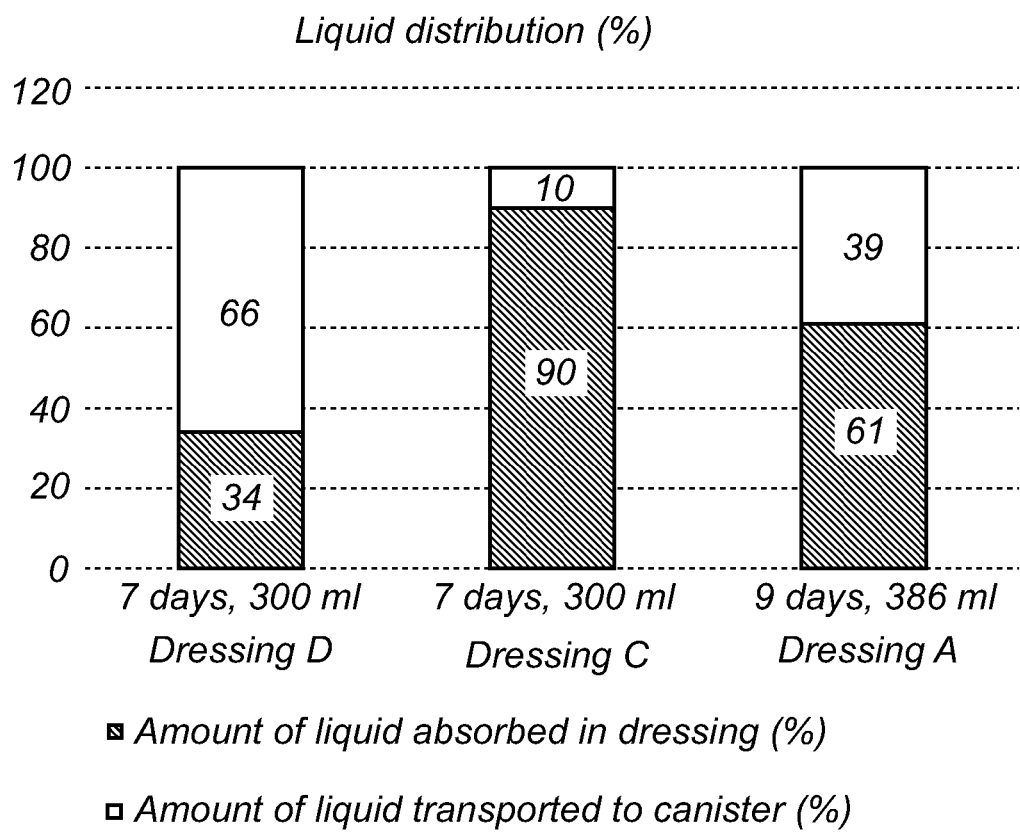
FIG. 4 illustrates the liquid distribution between the canister and three different absorbent dressings (Dressing D, Dressing C, and Dressing A, respectively).

The kit illustrated in FIG. 4 is adapted for home care, but is also advantageously used in a hospital or a care facility setting. The NPWT device is adapted to be carried by the user, e.g. in a pocket, belt, strap or similar. The dressing 100 and the other components of the kit 300 can easily be assembled by a user.

The components of the kit 300 may vary. For example, one kit may comprise all the components mentioned above, whereas others contain only two or three components.

The kit 300 may comprise a plurality of NPWT dressings as described herein before, optionally packaged together with a plurality of adhesive stripes.

Accordingly, the kit 300 comprises the negative pressure wound therapy dressing as described hereinbefore and at least one additional component, wherein the additional component is selected from a negative pressure source, a canister 117, a battery 124 and/or adhesive strip(s) 125.

The NPWT device 118 used in the kit (and in the NPWT system) of the present disclosure comprises the features and components necessary to control the operation of the device. For example, the NPWT device may comprise a control unit electrically connected to a battery. Such a control unit may comprise a microprocessor, microcontroller, programmable digital signal processor or another programmable device. In addition, the NPWT device 118 may comprise at least one pressure sensor arranged in fluid connection with the negative pressure pump.

EXAMPLES

Example 1: Liquid Distribution Comparative Tests

In order to test the distribution of liquid between the dressing and a canister, comparative tests were performed with three dressings (Dressing A, Dressing C, and Dressing D, respectively).

Dressing A comprised, from bottom-to-top, an adhesive skin contact layer comprising a polyurethane film and a silicone gel layer, a spacer fabric transmission layer, an absorbent structure (comprising a nonwoven liquid spreading layer, an airlaid SAP layer as described hereinbefore and a tissue layer), a nonwoven liquid spreading layer and a backing layer, respectively. Dressing C had the same layer construction as Dressing A, but the basis weight of the absorbent structure was higher, and the retention capacity and amount of superabsorbent particles per cm2 was different.

Dressing D had the same general layer construction, but differed with respect to the absorbent structure. The absorbent structure of Dressing D comprised an absorbent layer comprising 40% by weight of superabsorbent fibers (SAF) and 60% by weight of polyester (polyethylene terephthalate) fibers as well as a nonwoven spreading layer. No superabsorbent particles were present in the absorbent structure of Dressing D.

All dressings (A, C and D) comprised a pre-attached tubing comprising an air conduit and a fluid conduit.

Furthermore, all dressings (A, C and D) comprised a nonwoven liquid spreading layer arranged on top of the absorbent structure. The nonwoven liquid spreading layer comprised 50% by weight of viscose fibers and 50% by weight of bicomponent fibers. See table 1 below for more details on the dressings' absorbent structures.

TABLE 1

Absorption structure comparison

| | Dressing A | Dressing C | Dressing D |
|---|---|---|---|
| Spreading layers | Yes, two | Yes, two | Yes, one |
| Basis weight | 400 g/m2 | 600 g/m2 | 370 g/m2 |
| Retention capacity per cm2 dressing | 490 mg | 780 mg | 280 mg |
| Amount of SAP particles per cm2 absorbent structure | 15 mg | 24 mg | N/A |

The retention capacity was measured as described in Example 2, hereinafter.

Pre-weighed dressings were attached to a plexiglass plate of a larger size than the dressing area. The plexiglass plate had a hole for liquid inflow. The dressings were positioned so that the liquid inflow was in the middle portion of the dressing. Each dressing comprised a tubing that was connected to a mobile negative pressure device as illustrated in FIG. 2. The pump used was a pump of diaphragmatic type. A canister configured to store 50 ml of liquid was used and was connected to the pump arranged within a housing as disclosed in FIG. 2. The dressing and the NPWT device (comprising the canister and the pump) were connected by respective connector portions, as described hereinbefore. An air filter was arranged within the first connector portion associated with the dressing tubing. Ambient air was introduced into the connector and into the system such that the supply of air to the dressing was within the range of 2-7 ml/min. The pump was activated, and a negative pressure of −125 mmHg was applied to the dressings.

Test liquid (horse serum) was added in the middle of each dressing with a flow of 300 ml in 7 days (dressing C and D), and of 386 ml in 9 days (dressing A). The negative pressure in the dressing was maintained at −125 mmHg during the whole test period. After the test period, the wet weight of the dressings and the canister was recorded. The distribution of test liquid between each dressing and canister was calculated.

As can be seen in FIG. 4, the liquid distribution between dressing A and the canister was 61:39, whereas for dressing C, the majority of the liquid was kept in the dressing (90%) with only 10% being transferred to the canister. Dressing D had a dressing:canister liquid distribution of 34:66.

Figure 5A:
FIG. 5a is a picture of a first dressing (Dressing D) after exposure to test liquid during a test period of 7 days.

Pictures were also taken on the dressings after the test periods (7 days, and 9 days, respectively). As can be seen in FIG. 5a, Dressing D had a relatively poor liquid distribution within the dressing structure. In other words, only a small proportion of the absorbent capacity of the dressing was utilized. Instead, more exudate was transferred to the canister.

Figure 5B:
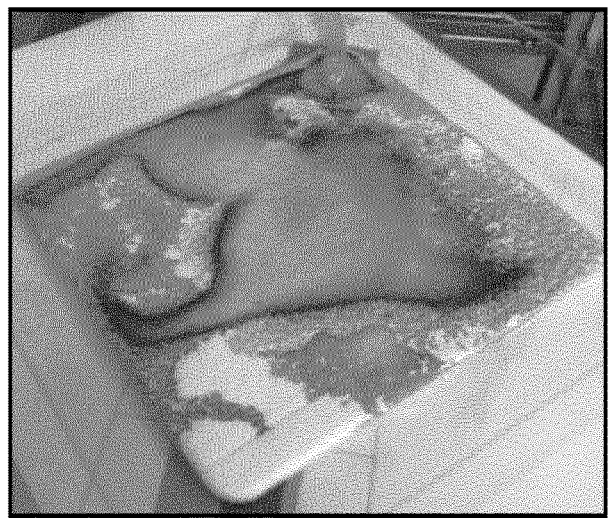
FIG. 5b is a picture of a second dressing (Dressing C) after exposure to test liquid during a test period of 7 days.

FIG. 5b illustrates Dressing C, where a large proportion of the dressing was utilized. Although not clearly visible from this figure, the dressing had a bulky and "soaky" appearance.

Figure 5C:
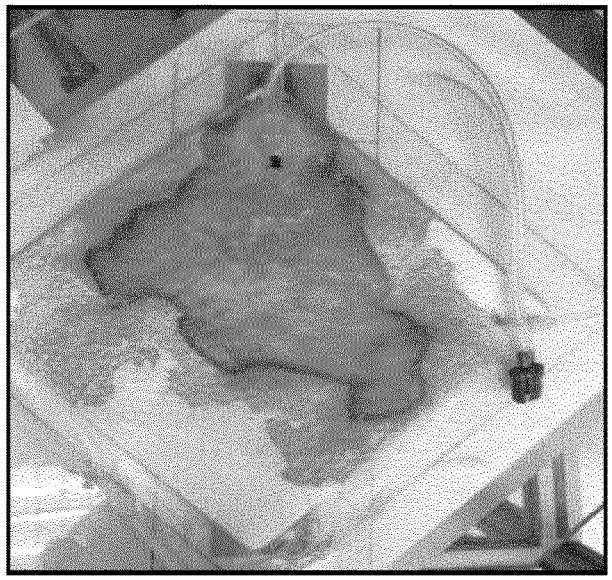
FIG. 5c is a picture of a third dressing (Dressing A) after exposure to test liquid during a test period of 9 days.

FIG. 5c illustrates Dressing A after 9 days of liquid exposure. A large proportion of the dressing was utilized for liquid handling, while still allowing for at least 39% of exudate to be transferred to the canister. A desired liquid distribution between the fluid collection means (dressing and canister) was thereby achieved.

Example 2: Retention Capacity of the Dressing

The fluid retention capacity is defined as the capability of dressing to retain liquid.

First, the theoretical maximum absorption was evaluated for the dressing samples. The maximum absorption capacity is the amount of liquid that the dressing is able to absorb when exposed to excess test liquid and in absence of an applied load.

Dressing samples A, C and D were punched to a pre-defined size (5×5 cm=25 cm²) from the central part of the dressing (such that all layers present in the dressing were used in the test).

The area and weight of the dressing samples (A, C and D) in a dry state were recorded. Each dressing sample was soaked in a bowl with a generous volume of test liquid (horse serum). A wire gauze was placed on top of the sample to force it down below the liquid surface, with the adhesive skin contact layer towards the wire gauze. Each sample was left to absorb for 60 minutes, covered with test liquid during the whole absorption time. When the absorption time was completed, the sample was hung vertically in one dressing corner to drain for 120 seconds. The samples were allowed to absorb liquid during 60 minutes. When the absorption time was completed, the specimens were drained freely for 120 seconds, held vertically in one corner (see figure below). The maximum absorption capacity was recorded in g liquid for each of the samples.

After the maximum absorption capacity had been calculated, a similar test was performed (as described above). The samples were allowed to absorb test liquid corresponding to 80% of the theoretical maximum absorption. After 10 minutes absorbing time, a pressure equivalent to 125 mmHg was added to the sample, with the wound side of the sample facing down. The static pressure was remained during 120 seconds. The retention was then calculated as the weight of horse serum retained in the sample after exposure to static pressure. The retention capacity is thus the ability of a product to hold liquid under a specified amount of pressure. The retention capacity for dressings A, C and D is illustrated in table 3 hereinbefore.

Example 3: Effect of Liquid Spreading Layer in Preventing Back-Flow of Liquid

In order to test the ability of the dressing to handle back-flow of exudate, which may be a problem when a dressing is disconnected from the NPWT device, a comparative test was set up with a dressing according to an exemplary embodiment of the present disclosure (Dressing A as described hereinbefore), and a reference dressing (Dressing E). Dressing E had the same construction as Dressing A, but lacked a nonwoven liquid spreading layer between the backing layer and the absorbent structure. The tubing of each dressing was connected to a mobile negative pressure device by means of the same procedure as described in Example 1.

Figure 6A:
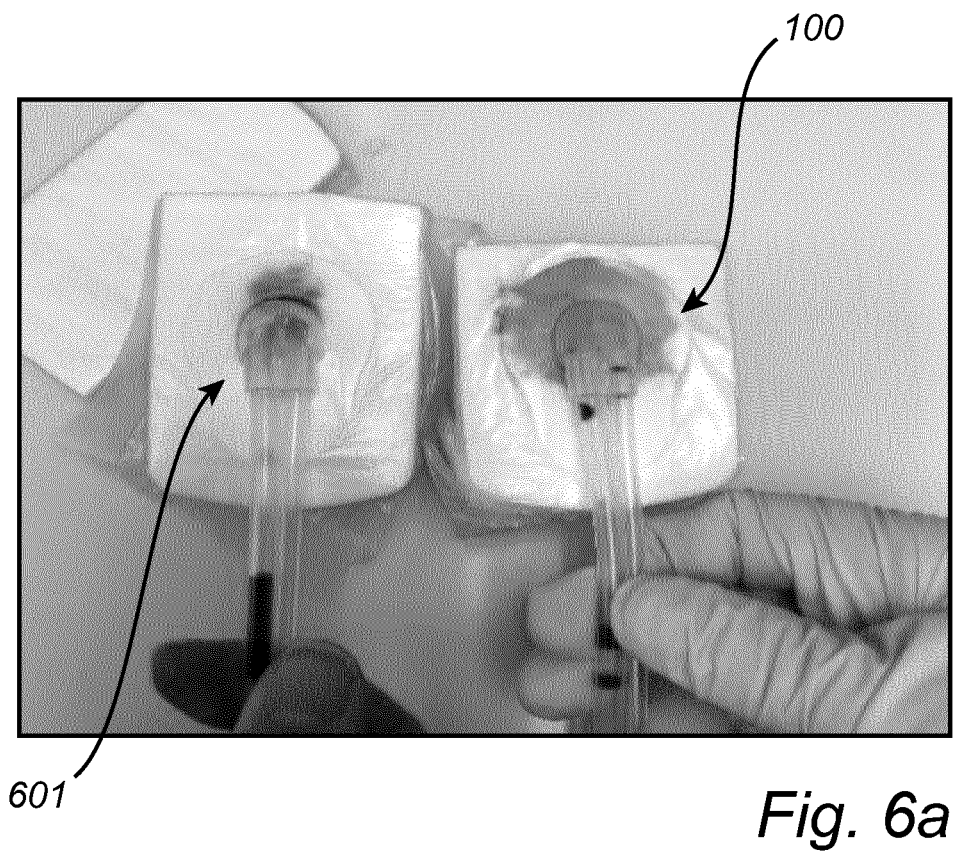
FIG. 6a illustrates pictures of a dressing according to an exemplary embodiment of the present disclosure (Dressing A) compared to a reference dressing (Dressing E), after exposure to liquid, as seen from the backing layer of the dressings.
Figure 6B:
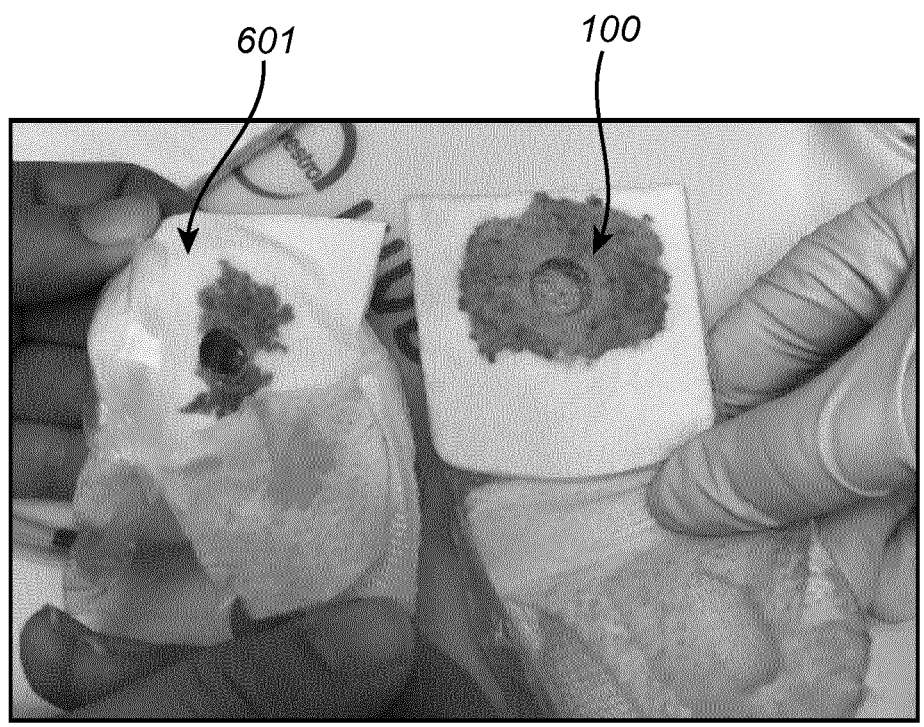
FIG. 6b illustrates pictures of a dressing according to an exemplary embodiment of the present disclosure (Dressing A) compared to a reference dressing (Dressing E), after exposure to liquid, as seen from the transmission layer, when the adhesive skin contact layer has been removed.

The canister was filled with approximately 52 ml horse serum (excess liquid). When the negative pressure of −125 mmHg was stable, the canister was disconnected from the pump and the excess liquid was transported back to the dressing. As can be seen in FIGS. 6a and 6b, the back-flow of exudate was distributed over a larger surface with a dressing of the present disclosure (Dressing A), denoted 100 in FIGS. 6a and 6b. In contrast, the back-flow of exudate in Dressing E (denoted 601 in FIGS. 6a and 6b), was not spread out to a significant degree, and a larger proportion of exudate was transferred directly back towards the wound site. The liquid spreading layer thereby contributes to an even exudate spreading and distribution in both directions.

Example 4: System Stability Comparative Tests

Wear tests were carried out utilizing two dressings (Dressing A, as described hereinbefore and Dressing B). Dressing A and Dressing B were similar in construction, and differed only with respect to the backing layer. Both dressings comprised a pre-attached tubing comprising an air conduit and a fluid conduit. The properties of the backing layer are listed in table 2 below.

TABLE 2

Backing layer material properties

|  | Dressing A | Dressing B |
| --- | --- | --- |
| Material | Polyurethane film | Polyurethane film |
| Thickness | 20 μm | 20 μm |
| MVTR | 2530 g/m²/24 h | 3940 g/m²/24 h |
| Tensile strength (MD) | 39 MPa/25 mm | 24 MPa/25 mm |
| Tensile strength (CD) | 37 MPa/25 mm | 24 MPa/25 mm |

The dressings were applied to the front knees of test subjects with the leg being bent at 120 degrees (the dressing tubing pointing upwards). The tubing was connected to a mobile negative pressure device by means of a respective connector portion as illustrated in FIG. 2. The pump used was pump of diaphragmatic type. A canister configured to store 50 ml of liquid, as disclosed in FIG. 1 was connected to the pump. The connector portion attached to the distal end of the dressing tubing comprised an air filter and ambient air was introduced into the connector such that the supply of air to the dressing (by means of the air conduit) was within the range of 2-7 ml/min during operation.

The pump was activated, and a negative pressure of −125 mmHg was applied to the dressings. The time between pump activations, Toff, was registered during the first five hours (0-5 hours, and 3-5 hours, respectively), which is an indication of the stability of the system and a means to secure that undesired air has not been introduced into the system.

Tests were performed on 5 subjects and the average Toff during time 0-5 hours, and 3-5 hours, was recorded.

Figure 7:
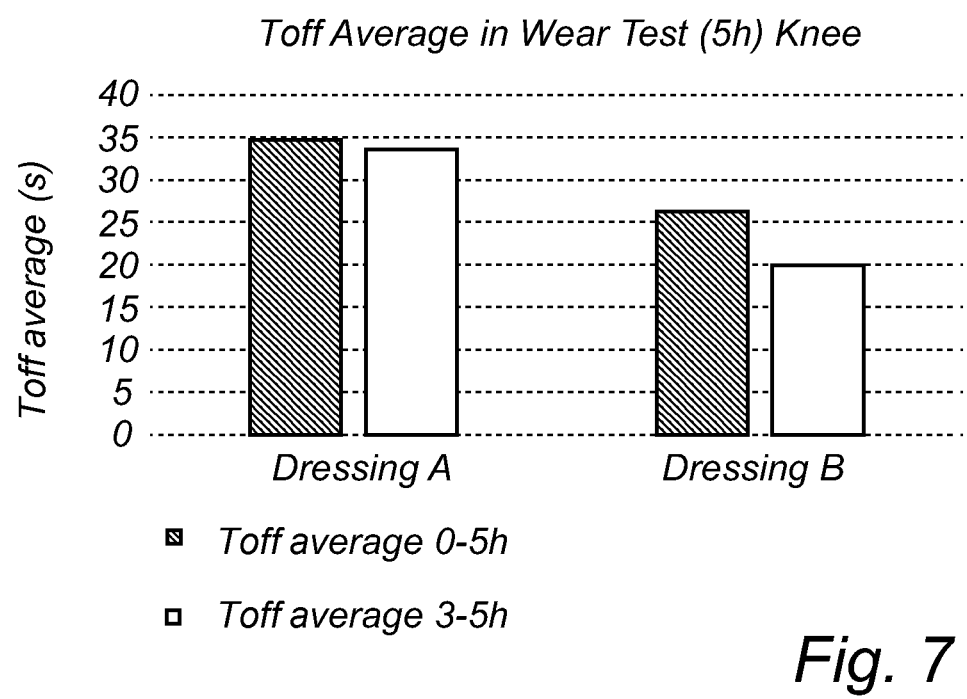
FIG. 7 illustrates the average time between pump activations, Toff, comparing two dressings (dressing A and dressing B) with backing layers having an MVTR of 2530 g/m2/24 h, and 3940 g/m$^2$/24 h, respectively.

The average Toff for dressing A was 35 seconds during time 0-5 hours compared to 26 seconds for dressing B, which is an improvement of 26%. The improvement was even more significant for the time 3-5 hours, where Toff was 40% higher for the dressing of the present disclosure. The results are illustrated in FIG. 7 and in table 3 below. These results indicate that properties of the backing layer have an impact on the stability of the negative pressure wound therapy. The system is stable and air-tight, and the pump does not need to work as hard.

TABLE 3

Average Toff comparison

|  | Dressing A | Dressing B |
| --- | --- | --- |
| Toff average 0-5 hours | 35 s | 26 s |
| Toff average 3-5 hours | 34 s | 20 s |

Terms, definitions and embodiments of all aspects of the present disclosure apply mutatis mutandis to the other aspects of the present disclosure.

Even though the present disclosure has been described with reference to specific exemplifying embodiments thereof, many different alterations, modifications and the like will become apparent for those skilled in the art.

Variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A negative pressure wound therapy (NPWT) system comprising:
    a dressing comprising:
        a backing layer comprising a coupling member, wherein the coupling member comprises tubing, wherein the tubing defines:
            a fluid conduit configured to remove fluid from said dressing; and
            an air conduit configured to supply air to said fluid conduit and/or said dressing,
        an adhesive skin contact layer,
        an absorbent structure arranged between said backing layer and said adhesive skin contact layer, wherein the absorbent structure comprises:
            a superabsorbent layer; and
            at least one additional liquid spreading layer, and
        a liquid spreading layer arranged between said absorbent structure and said backing layer;
        wherein said adhesive skin contact layer being configured to detachably adhere the dressing to a dermal surface,
    a NPWT device comprising:
        a pump;
        a remote fluid collection canister fluidly connected to said pump; and
        a battery operably coupled to the pump; and
    a length of tubing extending between a second connector portion and the NPWT device and fluidly coupling the pump and the remote fluid collection canister to the dressing,
    wherein the system is configured to receive an amount of liquid at the adhesive skin contact layer of the dressing during use, wherein the system is configured to distribute the amount of liquid between the dressing and the remote fluid collection canister such that at least 39%, but no more than 60% of the amount of liquid is collected by the remote fluid collection canister following 7 days of operation of the system with a negative pressure of −125 mmHg applied to the dressing.

2. The negative pressure wound therapy (NPWT) system according to claim 1, wherein said backing layer and at least a portion of said absorbent structure each comprises an opening; said opening of each of said absorbent structure and said backing layer being arranged underneath said coupling member, wherein said liquid spreading layer is void of an opening.

3. The negative pressure wound therapy (NPWT) system according to claim 1, wherein said liquid spreading layer is a configured to extend across at least 90% of a surface area of the absorbent structure.

4. The negative pressure wound therapy (NPWT) system according to claim 1, wherein said liquid spreading layer is a hydrophilic and porous layer.

5. The negative pressure wound therapy (NPWT) system according to claim 1, wherein said liquid spreading layer comprises a nonwoven.

6. The negative pressure wound therapy (NPWT) system according to claim 1, wherein said absorbent structure comprises superabsorbent particles in an amount of from 10 to 20 mg/cm$^2$.

7. The negative pressure wound therapy (NPWT) system according to claim 1, wherein the at least one additional liquid spreading layer comprises a first liquid spreading layer and a second liquid spreading layer, wherein said superabsorbent layer is arranged between said first and said second liquid spreading layers.

8. The negative pressure wound therapy (NPWT) system according to claim 7, wherein the first and second liquid spreading layers are in contact with the superabsorbent layer.

9. The negative pressure wound therapy (NPWT) system according to claim 1, wherein said absorbent structure is embossed.

10. The negative pressure wound therapy (NPWT) system according to claim 1, wherein said backing layer and said adhesive skin contact layer are configured to extend beyond a periphery of said absorbent structure to form a border portion along a contour of said absorbent structure, wherein said adhesive skin contact layer comprises a plurality of apertures in an area underlying said absorbent structure, but is void of apertures in an area forming said border portion.

11. The negative pressure wound therapy (NPWT) system according to claim 1, wherein said backing layer has a moisture vapor transmission rate (MVTR) in the range of from 500 to 3500 g/m$^2$/24 h, as measured by NWSP070.4R0 (15).

12. A kit comprising a negative pressure wound therapy (NPWT) system according to claim 1, and adhesive strip(s).

13. The negative pressure wound therapy (NPWT) system according to claim 1,
    wherein said dressing further comprises:
        a transmission layer arranged between said adhesive skin contact layer and said absorbent structure; and
        a plurality of adhesive stripes between said absorbent structure and said transmission layer, wherein the adhesive stripes are configured to inhibit a flow of exudate towards the coupling member,
    wherein said transmission layer comprises a spacer fabric.

14. The negative pressure wound therapy (NPWT) system according to claim 13, wherein the plurality of adhesive stripes are arranged orthogonal to a flow path of exudate towards the coupling member.

15. The negative pressure wound therapy (NPWT) system according to claim 13, wherein the plurality of adhesive stripes comprise between two and six adhesive stripes.

16. The negative pressure wound therapy (NPWT) system according to claim 1, wherein the coupling member comprises a first connector portion coupled to the fluid conduit and the air conduit, wherein the system further comprises the second connector portion detachably connected to said first connector portion to form a connector unit, wherein the second connector portion of the connector unit defines an air entry in communication with the air conduit, wherein the length of tubing extends between the second connector portion and the NPWT device.

17. The negative pressure wound therapy (NPWT) system according to claim 16, wherein the system is configured to supply air to said dressing at a rate of from 2 to 7 ml/min during operation.

18. The negative pressure wound therapy (NPWT) system according to claim 1, wherein the NPWT device is configured to be carried by a user during use.

* * * * *